(12) United States Patent
Pierce

(10) Patent No.: US 6,822,143 B2
(45) Date of Patent: Nov. 23, 2004

(54) CELERY NAMED ADS-1

(75) Inventor: Lawrence K. Pierce, Aromas, CA (US)

(73) Assignee: A. Duda & Sons, Inc., Ovieda, FL (US)

(*) Notice: Subject to any disclaimer, the term of this patent is extended or adjusted under 35 U.S.C. 154(b) by 0 days.

(21) Appl. No.: 10/277,396

(22) Filed: Oct. 21, 2002

(65) Prior Publication Data

US 2004/0078853 A1 Apr. 22, 2004

(51) Int. Cl.⁷ .............................. A01H 1/00; A01H 5/00; A01H 5/04; A01H 5/10; C12N 15/82
(52) U.S. Cl. .................... 800/318; 435/410; 800/260; 800/278; 800/279; 800/298; 800/300; 800/301; 800/302
(58) Field of Search ................................. 435/410, 430; 800/260, 268, 298, 318, 300, 301, 302, 278, 279

(56) References Cited

PUBLICATIONS

Browers and Orton 1986, Biotechnology in Agriculture and Forestry vol. 2: Crops I, edited by Y.P.S. Bajaj, Springer–Verlag, Berlin, Heidelberg, pp 405–420.*
Quiros et al 1987, Plant Cell Reports 6: 114–117.*
Quiros 1993, HortScience, 28(4): 250 and 359.*
US PVP Certificate #9800117 for Celery Named ADS–1.

* cited by examiner

*Primary Examiner*—David H Kruse
(74) *Attorney, Agent, or Firm*—Jondle & Associates P.C.

(57) ABSTRACT

A novel celery cultivar, designated ADS-1, is disclosed. The invention relates to the seeds of celery cultivar ADS-1, to the plants of celery line ADS-1 and to methods for producing a celery plant by crossing the cultivar ADS-1 with itself or another celery line. The invention further relates to methods for producing a celery plant containing in its genetic material one or more transgenes and to the transgenic plants produced by that method and to methods for producing other celery lines derived from the cultivar ADS-1.

15 Claims, No Drawings

CELERY NAMED ADS-1

BACKGROUND OF THE INVENTION

The present invention relates to a new and distinctive celery (*Apium graveolens* var. *dulce*) variety, designated ADS-1. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased stalk size and weight, higher seed yield, improved color, resistance to diseases and insects, tolerance to drought and heat, and better agronomic quality.

Practically speaking, all cultivated forms of celery belong to the species *Apium graveolens* var. *dulce* that is grown for its edible stalk. As a crop, celery is grown commercially wherever environmental conditions permit the production of an economically viable yield. In the United States, the principal growing regions are California, Florida, Texas and Michigan. Fresh celery is available in the United States year-round although the greatest supply is from November through January. For planting purposes, the celery season is typically divided into two seasons, summer and winter, with Florida, Texas and the southern California areas harvesting from November to July, and Michigan and northern California harvesting from July to October. Fresh celery is consumed as fresh, raw product and occasionally as a cooked vegetable.

Celery is a cool-season biennial that grows best from 60° to 65° F. (16° to 18° C.), but will tolerate temperatures from 45° to 75° F. (7° to 24° C.). Freezing will damage mature celery by splitting the petioles or causing the skin to peal, making the stalks unmarketable. This is an occasional problem in plantings in the winter regions. However, celery can tolerate minor freezes early in the crop.

The two main growing regions for celery (*Apium graveolens* L.) in California are located along the Pacific Ocean: the central coast or summer production area (Monterey, San Benito, Santa Cruz and San Luis Obispo Counties) and the south coast or winter production area (Ventura and Santa Barbara Counties). A minor region (winter) is located in the southern deserts (Riverside and Imperial Counties).

In the south coast, celery is transplanted from early August to April for harvest from November to mid-July; in the Santa Maria area, celery is transplantaed from January to August for harvest from April through December. In the central coast, fields are transplanted from March to September for harvest from late June to late December. In the southern deserts, fields are transplanted in late August for harvest in January.

Commonly used celery varieties for coastal production include Tall Utah 52-75, Conquistador and Sonora. Some shippers use their own proprietary varieties. Celery seed is very small and difficult to germinate. All commercial celery is planted as greenhouse-grown transplants. Celery grown from transplants is more uniform than from seed and takes less time to grow the crop in the field. Transplanted celery is placed in double rows on 40-inch (100-cm) beds with plants spaced between 6.7 and 7 inches (22.5-cm) apart.

Celery is an allogamous biennial crop. Celery consists of 11 chromosomes. Its high degree of out-crossing is accomplished by insects and wind pollination. Pollinators visiting celery flowers include a large number of wasp, bee and fly species. Celery is subject to inbreeding depression, which appears to be genotype dependent, since some lines are able to withstand continuous selfing for three or four generations. Crossing of inbreds results in heterotic hybrids that are vigorous and taller than sib-mated or inbred lines.

Celery flowers are protandrous, with pollen being released 3–6 days before stigma receptivity. At the time of stigma receptivity the stamens will have fallen and the two stigmata unfolded in an upright position. The degree of protandy varies, which makes it difficult to perform reliable hybridization, due to the possibility of accidental selfing.

Celery flowers are very small, significantly precluding easy removal of individual anthers. Furthermore, different developmental stages of the flowers in umbels makes it difficult to avoid uncontrolled pollinations. The standard hybridization technique in celery consists of selecting flower buds of the same size and eliminating the older and younger flowers. Then, the umbellets are covered with glycine paper bags for a 5–10 day period, during which the stigmas become receptive. At the time the flowers are receptive, available pollen or umbellets shedding pollen from selected male parents are rubbed on to the stigmas of the female parent.

Plants require a period of vernalization while in the vegetative phase in order to induce seed stalk development. A period of 6–10 weeks at 5–8° C. is usually adequate. However, unless plants are beyond a juvenile state or a minimum of 4 weeks old they may not be receptive to vernalization. Due to a wide range of response to the cold treatment, it is often difficult to synchronize crossing, since plants will flower at different times. However, pollen can be stored for 6–8 months at –10° C. in the presence of silica gel or calcium chloride with a viability decline of only 20–40%, thus providing flexibility to perform crosses over a longer time.

For selfing, the plant or selected umbels are caged in cloth bags. These are shaken several times during the day to promote pollen release. Houseflies (*Musca domestica*) can also be introduced weekly into the bags to perform pollinations.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from ten to twenty years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior celery cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same celery traits.

Each year, the plant breeder selects the germplasm to advance to the next generation. This germplasm is grown under unique and different geographical, climatic and soil conditions, and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior celery cultivars.

The development of commercial celery cultivars requires the development of celery varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits, are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population, will be represented by a progeny when generation advance is completed Descriptions of other breeding methods that are commonly used for different traits and crops can be found in one of several reference books (e.g., "Principles of Plant Breeding" John Wiley and Son, pp. 115–161, 1960; Allard, 1960; Simmonds, 1979; Sneep et al., 1979; Fehr, 1987; "Carrots and Related Vegetable Umbelliferae", Rubatzky, V. E., et al., 1999).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Celery in general is an important and valuable vegetable crop. Thus, a continuing goal of plant breeders is to develop stable, high yielding celery cultivars that are agronomically sound. The reasons for this goal are obviously to maximize the amount of yield produced on the land. To accomplish this goal, the celery breeder must select and develop celery plants that have the traits that result in superior cultivars.

SUMMARY OF THE INVENTION

According to the invention, there is provided a novel celery cultivar, designated ADS-1. This invention thus relates to the seeds of celery cultivar ADS-1, to the plants of celery cultivar ADS-1 and to methods for producing a celery plant produced by crossing the celery ADS-1 with itself or another celery line, and to methods for producing a celery plant containing in its genetic material one or more transgenes and to the transgenic celery plants produced by that method. This invention also relates to methods for producing other celery cultivars derived from celery cultivar ADS-1 and to the celery cultivar derived by the use of those methods. This invention further relates to hybrid celery seeds and plants produced by crossing the line ADS-1 with another celery line.

In another aspect, the present invention provides regenerable cells for use in tissue culture of celery cultivar ADS-1. The tissue culture will preferably be capable of regenerating plants having the physiological and morphological characteristics of the foregoing celery plant, and of regenerating plants having substantially the same genotype as the foregoing celery plant. Preferably, the regenerable cells in such tissue cultures will be embryos, protoplasts, seeds, callus, pollen, leaves, anthers, roots, suckers and meristematic cells. Still further, the present invention provides celery plants regenerated from the tissue cultures of the invention.

Another objective of the invention is to provide methods for producing other celery plants derived from celery cultivar ADS-1. Celery cultivars derived by the use of those methods are also part of the invention.

The invention also relates to methods for producing a celery plant containing in its genetic material one or more transgenes and to the transgenic celery plant produced by that method.

In another aspect, the present invention provides for single gene converted plants of ADS-1. The single transferred gene may preferably be a dominant or recessive allele. Preferably, the single transferred gene will confer such trait as male sterility, herbicide resistance, insect resistance, resistance for bacterial, fungal, or viral disease, male fertility, enhanced nutritional quality and industrial usage. The single gene may be a naturally occurring celery gene or a transgene introduced through genetic engineering techniques.

The invention further provides methods for developing celery plant in a celery plant breeding program using plant breeding technique including recurrent selection, backcrossing, pedigree breeding, restriction fragment length polymorphism enhanced selection, genetic marker enhanced selection and transformation. Seeds, celery plant, and parties thereof produced by such breeding methods are also part of the invention.

DEFINITIONS

In the description and tables which follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of a line are recovered in addition to the single gene transferred into the line via the backcrossing technique or via genetic engineering.

Maturity Date. Maturity in celery can be dictated by two conditions. The first, or true maturity, is the point in time when the celery reaches maximum size distribution, but before defects such as pith, yellowing, feather-leaf or brownstem appear. The second, or market maturity is an artificial maturity dictated by market conditions, i.e, the market requirement may be for 3 dozen sizes so the field is harvested at slightly below maximum yield potential because the smaller sizes are what the customers prefer at that moment.

RHS. RHS refers to the Royal Horticultural Society of England which publishes an official botanical color chart quantitatively identifying colors according to a defined numbering system, The chart may be purchased from Royal Hort Society Enterprise Ltd RHS Garden; Wisley, Woking; Surrey GU236QB, UK.

Celery Yield (Tons/Acre). The yield in tons/acre is the actual yield of the celery at harvest.

Theoretical Maximum Yield. If you assume 100% 2 dozen size and a 47,000 plant population per acre and 70 pound cartons, your theoretical maximum yield would be 68.5 tons.

DETAILED DESCRIPTION OF THE INVENTION

ADS-1 is probably the first variety to be developed specifically for high population (density) production. Normal production is a 45,000 to 47,000 plant population. At a 65,000 plant population ADS-1 produces the same size range of plants that it does at the lower density while other varieties produce smaller celery and many that are not harvestable. At a density of 75,000 it still performs quite well, out yielding all other varieties.

ADS-1 generally has a more uniform joint placement compared to other varieties including Gene's Gem 12. ADS-1 is different from other varieties on the market because ADS-1 is higher for overall sugars and Vitamin C. ADS-1 is especially high for sucrose. ADS-1 is consistently sweeter to the taste than other celery varieties. ADS-1 is generally less stringy. The strings on ADS-1 are larger and much more brittle and were quite a bit deeper in the petiole versus other varieties, except Gene's Gem 12.

ADS-1 is similar to Gene's Gem 12 for color and as dark as Conquistador, Sonora and Tall Utah 52-75. ADS-1 performs better than Gene's Gem 12 under conditions of *Fusarium oxysporum* f.v. apii race 2.

Some of the criteria used to select in various generations include: color, disease resistances, stalk weight, number of leaves, appearance and length, yield, emergence, maturity, plant architecture, seed yield and quality, and disease resistance.

The cultivar has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in ADS-1.

Celery cultivar ADS-1 has the following morphologic and other characteristics (based primarily on data collected at Salinas, California Research Station and field plots).

| VARIETY DESCRIPTION INFORMATION | |
| --- | --- |
| Plant Height: | 82.4 cm |
| Number of Outer Petioles (>40 cm): | 12.7 |
| Number of Inner Petioles (<40 cm): | 10.9 |
| Length of Outer Petioles @ Joint: | 30.4 cm |
| Width of Outer Petioles @ midrib: | 26.5 mm |
| Thickness of Outer Petioles @ midrib: | 11.9 mm |
| Petiole Color: | 5GY 7/6 |
| Leaf Color: | 5GY 3/4 |
| Petiole Type: | Smooth, deeply cupped |

TABLES

In the tables that follow, the traits and characteristics of celery cultivar ADS-1 are given compared to other check cultivars.

Table 1 shows a yield comparison between Gene's Gem 12 at standard density and ADS-1 at both standard and high density. Gene's Gem 12 was not included in this larger acreage planting test at higher density yields because the yield of Gene's Gem 12 would not compensate for the higher cost of production. Theoretical maximum yield calculations have been incorporated in order to establish a baseline for maximum potential yield. Celery is packed based on stalk size. Theoretical Maximum Yield is determined for 100% yield of one particular size and a known plant population.

Table 1 shows ADS-1 has better yield than Gene's Gem 12 at a standard plant population (47,000). It is also apparent that increasing the population of ADS-1 from 47,000 to 65,000 had no apparent affect on the distribution of large celery sizes; 2 dozen and 2½ dozen sizes were still harvested at the same ratio. Carton weight was also relatively unaffected.

TABLE 1

Yield Comparison Between ADS-1 and Gene's Gem 12 under Standard Density and ADS-1 Under High Density

| Variety | Gene's Gem 12 | ADS-1 | ADS-1 |
| --- | --- | --- | --- |
| Density | Standard (47,000 plants/acre) | Standard (47,000 plants/acre) | High (65,000 plants/acre) |
| Spacing | 2 lines/40" bed | 2 lines/40" bed | 3 lines/40" bed |
| Theoretical Maximum Yield | | | |
| 100% 2's | 1,958 | 1,958 | 2,708 |
| 100% 2 1/2's | 1,566 | 1,566 | 2,166 |
| Actual Yield | | | |
| Total Cartons | 1,568 | 1,608 | 2,197 |

TABLE 1-continued

Yield Comparison Between ADS-1 and Gene's Gem 12 under Standard Density and ADS-1 Under High Density

| Variety | Gene's Gem 12 | ADS-1 | ADS-1 |
| --- | --- | --- | --- |
| % 2's | 55 | 60 | 60 |
| % 2 1/2's | 23 | 18 | 18 |
| Carton Weight | 66# | 70# | 67–68# |

Table 2 shows yield comparisons between ADS-1, Gene's Gem 12, Conquistador and Sonora under standard density production conditions (47,000 plants per acre), planted on two rows on 40 inch bed. The total acreage for each variety varies, but the yield per acre compensates for this variation. This data is broken down as percent of large and small sizes. Large size generally refers to everything larger or equal to 2½ dozen, i.e., 1.5, 2 and 2.5 dozen stalks per carton. Three dozen or smaller are in the smaller size classification (3, 4 and 6 dozen per carton).

Gene's Gem 12 and ADS-1 both produced a few 1½ dozen cartons as well as the heaviest cartons overall. ADS-1 produced the highest yield per acre, the highest percentage of large sizes and is generally slightly longer to the joint.

TABLE 1

Yield of ADS-1 Compared to Other Varieties Grown at Standard Density (47,000 Plants per Acre)

| Variety | Harvest'd Acres | Total Yield Cartons | Yield/Acre Cartons | Percent Large Sizes | Large Size Range | Percent Small Sizes | Avg Wt Carton (lbs) | Joint Length Range (inches) |
| --- | --- | --- | --- | --- | --- | --- | --- | --- |
| ADS-1 | 1.44 | 2047 | 1421 | 71% | 1.5/2/2.5 | 29% | 63–65 | 11–13 |
| Gene's Gem 12 | 1.68 | 2268 | 1350 | 65% | 1.5/2/2.5 | 35% | 62–63 | 9–12 |
| Sonora | 1.45 | 1943 | 1340 | 62% | 2/2.5 | 38% | 53–55 | 10–12 |
| Conquistador | 1.62 | 2134 | 1317 | 67% | 2/2.5 | 33% | 54–56 | 10–13 |

Tables 3A and 3B show yield comparisons between ADS-1, Gene's Gem 12, Conquistador, Tall Utah 52-75 and Sonora under high density production conditions (65,000 plants per acre). ADS-1 had higher yields and a greater percentage of larger sizes at the higher plant population. Table 3B shows that ADS-1 is almost 100% harvestable at this population while the other varieties do not perform as well (many of the plants never make enough size to be harvested).

Normal celery production is 2 rows on a 40 inch bed at 47,000 plants per acre. High density in this instance is 3 rows on a 40 inch bed planted at a population of 65,000 plants per acre.

Celery is packed by size. 2's=2 dozen stalks per carton; 2.5's=30 stalks per carton, 3's=3 dozen per carton; 4's=4 dozen stalks per carton. Weight in each category is the average weight of a carton in each category. % size is the percentage of total cartons that the size represents. Total yield per acre is the total cartons for all sizes harvested for the variety.

TABLE 3A

Yield Comparisons of ADS-1 and Other Varieties Under High Density Conditions

| Varieties | 2's Wt. | 2's Yld/Acre | 2's % Size | 2.5's Wt. | 2.5's Yld/Acre | 2.5's % Size | 3's Wt. | 3's Yld/Acre | 3's % Size | 4's Wt. | 4's Yld/Acre | 4's % Size | Total Yield/acre |
|---|---|---|---|---|---|---|---|---|---|---|---|---|---|
| ADS-1 | 57 | 98 | 5% | 55 | 1369 | 67% | 60 | 391 | 19% | 60 | 147 | 10% | 2005 |
| Gene's Gem 12 | 55 | 98 | 5% | 55 | 978 | 58% | 54 | 489 | 16% | 55 | 293 | 21% | 1858 |
| Conquistador |  |  |  | 55 | 782 | 47% | 55 | 684 | 41% | 60 | 196 | 12% | 1662 |
| Tall Utah 52–75 |  |  |  | 59 | 489 | 33% | 55 | 684 | 47% | 58 | 293 | 20% | 1466 |
| Sonora |  |  |  | 55 | 978 | 58% | 55 | 489 | 26% | 55 | 293 | 16% | 1760 |

TABLE 3B

Comparison of Harvest Efficiency Between ADS-1 and Other Varieties Under Conditions of High Density

| Varieties | Total Plants Harvested/Acre | % Plants Marketable |
|---|---|---|
| ADS-1 | 64538 | 96% |
| Gene's Gem 12 | 63365 | 94% |
| Conquistador | 57492 | 77% |
| Tall Utah 52–75 | 53358 | 71% |
| Sonora | 61001 | 81% |

Tables 4A and 4B show yield comparisons between ADS-1, Gene's Gem 12, Conquistador and Sonora under very high density production conditions (75,000 plants per acre). This yield trial also shows yields and carton weight taken for each size. It is obvious that ADS-1 had higher yields and a greater percentage of larger sizes at this very high plant population. The smaller table also shows that ADS-1 is almost 100% harvestable at this population while the other varieties do not perform as well (many of the plants never make enough size to be harvested).

TABLE 4A

Yield Comparisons of ADS-1 and Other Varieties Under Very High Density Conditions

| Varieties | 2's Wt. | 2's Yld/Acre | 2's % Size | 2.5's Wt. | 2.5's Yld/Acre | 2.5's % Size | 3's Wt. | 3's Yld/Acre | 3's % Size | 4's Wt. | 4's Yld/Acre | 4's % Size | Total Yield/acre |
|---|---|---|---|---|---|---|---|---|---|---|---|---|---|
| ADS-1 | 50 | 614 | 27% | 59 | 614 | 27% | 59 | 844 | 37% | 55 | 230 | 10% | 2302 |
| Gene's Gem 12 | 55 | 423 | 22% | 55 | 762 | 39% | 60 | 508 | 28% | 55 | 254 | 13% | 1946 |
| Conquistador | 53 | 275 | 14% | 53 | 510 | 26% | 63 | 653 | 34% | 54 | 367 | 19% | 1925 |
| Sonora | 53 | 289 | 15% | 60 | 618 | 32% | 56 | 726 | 37% | 59 | 314 | 16% | 1947 |

TABLE 4B

Comparison of Harvest Efficiency Between ADS-1 and Other Varieties Under Conditions of Very High Density

| Varieties | Total Yield | Total Plants Harvested/Acre | % Plants Marketable |
|---|---|---|---|
| ADS-1 | 2302 | 74580 | 99% |
| Gene's Gem 12 | 1946 | 63492 | 85% |
| Conquistador | 1925 | 63024 | 84% |
| Sonora | 1947 | 66684 | 89% |

Tables 5A and 5B: This trial is similar to that shown in tables 4A and 4B and includes additional varieties.

TABLE 5A

Yield Comparisons of ADS-1 and Other Varieties Under Very High Density Conditions

| Varieties | 2's Wt. | 2's Yld/Acre | 2's % Size | 2.5's Wt. | 2.5's Yld/Acre | 2.5's % Size | 3's Wt. | 3's Yld/Acre | 3's % Size | 4's Wt. | 4's Yld/Acre | 4's % Size | Total Yield/acre |
|---|---|---|---|---|---|---|---|---|---|---|---|---|---|
| ADS-1 | 55 | 990 | 41% | 55 | 770 | 32% | 63 | 440 | 18% | 55 | 220 | 9% | 2420 |
| Gene's Gem 12 | 56 | 770 | 41% | 65 | 770 | 41% | 59 | 220 | 12% | 58 | 110 | 6% | 1870 |
| Conquistador | 56 | 73 | 5% | 57 | 660 | 43% | 54 | 587 | 38% | 56 | 220 | 14% | 1540 |
| Tall Utah 52–75 | 57 | 513 | 28% | 53 | 513 | 28% | 56 | 513 | 28% | 59 | 293 | 16% | 1833 |
| Sonora | 55 | 73 | 4% | 55 | 733 | 42% | 55 | 660 | 38% | 57 | 293 | 17% | 1760 |
| Hill's Special | 55 | 157 | 11% | 59 | 471 | 32% | 55 | 629 | 42% | 59 | 236 | 16% | 1493 |

TABLE 5B

Comparison of Harvest Efficiency Between ADS-1 and Other Varieties Under Conditions of Very High Density

| Varieties | Total Plants Harvested/Acre | % Plants Marketable |
|---|---|---|
| ADS-1 | 73260 | 98% |
| Gene's Gem 12 | 54780 | 73% |
| Conquistador | 53240 | 71% |
| Tall Utah 52–75 | 60280 | 80% |
| Sonora | 61600 | 82% |
| Hill's Special | 51857 | 69% |

Table 6A and 6B show the results of a nutritional test run on ADS-1, Conquistador, Sonora and Tall Utah 52-75. The standard USDA label information is included for reference. ADS-1 tested higher for Vitamin C and overall sugars. A further test of individual sugars showed that fructose was generally higher in ADS-1 and ADS-1 was the only variety with sucrose. ADS-1 also proved considerably higher for sweetness when the sweetness equivalent of each sugar is considered. Sweetness equivalency is based on the following sweetness ratings: Fructose has a sweetness rating of 140; Glucose has a sweetness rating of 70–80 and Sucrose has a sweetness rating of 100.

TABLE 6A

Label Values for Constituents of the Various Varieties

| | USDA Celery Label Label Amt 110 g | USDA Celery Label RDA % 110 g | ADS-1 Label Amt 110 g | ADS-1 RDA % 110 g | Conquistador Label Amt 110 g | Conquistador RDA % 110 g | Sonora Label Amt 110 g | Sonora RDA % 110 g | Tall Utah 52–75 Label Amt 110 g | Tall Utah 52–75 RDA % 110 g |
|---|---|---|---|---|---|---|---|---|---|---|
| Total Carbo. | 5 g | 2% | 6 g | 2% | 5 g | 2% | 5 g | 2% | 5 g | 2% |
| Dietary Fiber | 2 g | 8% | 4 g | 17% | 4 g | 17% | 4 g | 17% | 4 g | 17% |
| Sugars | 1 g | | 2 g | | 1 g | | 1 g | | 1 g | |
| Vitamin C | | 15% | | 22% | | 15% | | 12% | | 16% |

TABLE 6B

Sugar Details

| | USDA Celery Label Label Amt 110 g | ADS-1 Label Amt 110 g | Conquistador Label Amt 110 g | Sonora Label Amt 110 g | Tall Utah 52–75 Label Amt 110 g |
|---|---|---|---|---|---|
| Fructose | | 0.4766 | 0.3634 | 0.4209 | 0.4120 |
| Glucose | | 0.9440 | 0.9792 | 0.7593 | 0.7003 |
| Sucrose | | 0.2355 | 0.0000 | 0.0000 | 0.0000 |
| Total Sugar | | 1.6561 | 1.3426 | 1.1802 | 1.1123 |
| Label Value | 1 g | 2 g | 1 g | 1 g | 1 g |
| Sweetness equivalent | ? | 161 | 124 | 116 | 110 |

Table 7: One of the main customer complaints for celery is stringiness. Because the strings are actually the vascular bundles it is impossible to remove them. Larger vascular bundles are more fragile and tend to break much easier. These vascular bundles are especially easily broken if they are deeper in the petiole.

TABLE 7

Vascular Bundle Measurements as an Indicator of Stringyness

| Variety | Vascular Bundle Depth Below Petiole Surface (mm) | Vascular Bundle Thickness (mm) |
| --- | --- | --- |
| ADS-1 | 3.11 (Range - 2.56–4.01) | 0.93 (Range - 0.78–1.10) |
| Gene's Gem 12 | 2.90 (Range - 2.50–3.48) | 1.03 (Range - 0.85–1.15) |
| Conquistador | 1.65 (Range - 1.41–2.00) | 0.70 (Range - 0.52–0.79) |
| Sonora | 1.55 (Range - 1.32–1.77) | 0.69 (Range - 0.53–0.82) |
| Promise | 2.01 (Range - 1.50–2.44) | 0.73 (Range - 0.64–0.82) |
| Ponderosa | 2.06 (Range - 1.87–2.41) | 0.72 (Range - 0.65–0.75) |
| Tall Utah 52–70 'R' Strain | 1.91 (Range - 1.54–2.57) | 0.77 (Range - 0.65–0.95) |
| Hill's Special | 2.20 (Range - 1.99–2.39) | 0.68 (Range - 0.50–0.82) |
| Tall Utah 52–75 | 1.66 (Range - 1.20–1.94) | 0.62 (Range - 0.46–0.80) |

FURTHER EMBODIMENTS OF THE INVENTION

This invention also is directed to methods for producing a celery cultivar plant by crossing a first parent celery plant with a second parent celery plant wherein either the first or second parent celery plant is a celery plant of the line ADS-1. Further, both first and second parent celery plants can come from the cultivar ADS-1. Still further, this invention also is directed to methods for producing a cultivar ADS-1-derived celery plant by crossing cultivar ADS-1 with a second celery plant and growing the progeny seed, and repeating the crossing and growing steps with the cultivar ADS-1-derived plant from 0 to 7 times. Thus, any such methods using the cultivar ADS-1 are part of this invention: selfing, backcrosses, hybrid production, crosses to populations, and the like. All plants produced using cultivar ADS-1 as a parent are within the scope of this invention, including plants derived from cultivar ADS-1. Advantageously, the cultivar is used in crosses with other, different, cultivars to produce first generation ($F_1$) celery seeds and plants with superior characteristics.

As used herein, the term plant includes plant cells, plant protoplasts, plant cell tissue cultures from which celery plants can be regenerated, plant calli, plant clumps and plant cells that are intact in plants or parts of plants, such as embryos, pollen, ovules, flowers, seeds, roots, anthers, suckers and the like.

As is well known in the art, tissue culture of celery can be used for the in vitro regeneration of a celery plant. Tissue culture of various tissues of celerys and regeneration of plants therefrom is well known and widely published. For example, reference may be had to Teng et al., *HortScience.* 1992, 27: 9, 1030–1032 Teng et al., *HortScience.* 1993, 28: 6, 669–1671, Zhang et al., *Journal of Genetics and Breeding.* 1992, 46: 3, 287–290, Webb et al., *Plant Cell Tissue and Organ Culture.* 1994, 38: 1, 77–79, Curtis et al., *Journal of Experimental Botany.* 1994, 45: 279, 1441–1449, Nagata et al., *Journal for the American Society for Horticultural Science.* 2000, 125: 6, 669–672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce celery plants having the physiological and morphological characteristics of variety ADS-1.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed line.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed celery plants, using transformation methods as described below to incorporate transgenes into the genetic material of the celery plant(s).

Expression Vectors for Celery Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990<Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

Recently, in vivo methods for visualizing GUS activity that do not require destruction of plant tissue have been made available. Molecular Probes publication 2908, Imagene Green™, p. 1–4 (1993) and Nalewayetal., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in celery. Optionally, the inducible promoter is operably linked to a nucleotide sequence encoding a signal sequence which is operably linked to a gene for expression in celery. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in celery or the constitutive promoter is operably linked to a nucleotide sequence encoding a signal sequence which is operably linked to a gene for expression in celery.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/NcoI fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-Specific or Tissue-Preferred Promoters

A tissue-specific promoter is operably linked to a gene for expression in celery. Optionally, the tissue-specific promoter is operably linked to a nucleotide sequence encoding a signal sequence which is operably linked to a gene for expression in celery. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is celery. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology *CRC Press, Boca Raton* 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* á-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect *Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung celery calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a celery endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

R. A lettuce mosaic potyvirus (LMV) coat protein gene introduced into Lactuca Sativa in order to increase its resistance to LMV infection. See Dinant et al., Molecular Breeding. 1997, 3: 1, 75–86.

2. Genes that Confer Resistance to a Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in *Transgenic Research*. 1999, 8: 1, 33–44 that discloses lactuca sativa resistant to glufosinate. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Increased iron content of the celery, for example by transforming a plant with a soybean ferritin gene as decribed in Goto et al., *Acta Horticulturae*. 2000, 521, 101–109. Parallel to the improved iron content enhanced growth of transgenic celerys was also observed in early development stages.

B. Decreased nitrate content of leaves, for example by transforming a celery with a gene coding for a nitrate reductase. See for example Curtis et al., *Plant Cell Report*. 1999, 18: 11, 889–896.

C. Increased sweetness of the celery by transferring a gene coding for monellin, that elicits a flavor 100000 times sweeter than sugar on a molar basis. See Penarrubia et al., *Biotechnology*. 1992, 10: 5, 561–564.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-Mediated Transformation

One method for introducing an expression vector into plants is based on the natural transformation system of Agrobacterium. See, for example, Horsch et al., *Science* 227:1229 (1985). Curtis et al., *Journal of Experimental Botany*. 1994, 45: 279, 1441–1449, Torres et al., *Plant cell Tissue and Organic Culture*. 1993, 34: 3, 279–285, Dinant et al., *Molecular Breeding*. 1997, 3: 1, 75–86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Despite the fact the host range for Agrobacterium-mediated transformation is broad, some major cereal or vegetable crop species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectilemediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Russell, D. R., et al. *Pl. Cell. Rep.* 12(3, Jan.), 165–169 (1993), Aragao, F. J. L., et al. *Plant Mol. Biol.* 20(2, Oct.), 357–359 (1992), Aragao, F. J. L., et al. *Pl. Cell. Rep.* 12(9, July), 483–490 (1993). Aragao *Theor. Appl. Genet.* 93: 142–150 (1996), Kim, J.; Minamikawa, T. *Plant Science* 117: 131–138 (1996), Sanford et al., *Part. Sci. Technol.* 5:27 (1987), Sanford, J. C., *Trends Biotech*. 6:299 (1988), Klein et al., *Bio/Technology* 6:559–563 (1988), Sanford, J. C., *Physiol Plant* 7:206 (1990), Klein et al., *Biotechnology* 10:268 (1992)

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A*. 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Saker, M.; Kuhne, T. *Biologia Plantarum* 40(4): 507–514 (1997/98), Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994). See also Chupean et al., *Biotechnology*. 1989, 7: 5, 503–508.

Following transformation of celery target tissues, expression of the abovedescribed selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic celery line. Alternatively, a genetic trait which has been engineered into a particular celery cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term celery plant, cultivar or celery line are used in the context of the present invention, this also includes any single gene conversions of that line. The term single gene converted plant as used herein refers to those celery plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term backcrossing as used herein refers to the repeated crossing of a hybrid progeny back to one of the parental celery plants for that line. The parental celery plant which contributes the gene for the desired characteristic is termed the nonrecurrent or donor parent. This terminology refers to the fact that the nonrecurrent parent is used one time in the backcross protocol and therefore does not recur. The parental celery plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a celery plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196; 5,948,957 and 5,969,212, the disclosures of which are specifically hereby incorporated by reference.

DEPOSIT INFORMATION

A deposit of the A. Duda & Sons, Inc. proprietary celery named ADS-1 disclosed above and recited in the appended claims has been made with the American Type Culture Collection (ATCC), 10801 University Boulevard, Manassas, Va. 20110. The date of deposit was Jun. 4, 2004. The deposit of 2,500 seeds was taken from the same deposit maintained by A. Duda & Sons, Inc. since prior to the filing date of this application. All restrictions upon the deposit have been removed, and the deposit is intended to meet all of the requirements of 37 C.F.R. §1.801–1.809. The ATCC accession number is PTA-6041. The deposit will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant line and the like may be practiced within the scope of the invention, as limited only by the scope of the appended claims.

What is claimed is:

1. Seed of a celery variety designated ADS-1, representative seed having been deposited under ATCC Accession No. PTA-6041.

2. A celery plant, or parts thereof, produced by growing the seed of claim 1.

3. Pollen of the plant of claim 2.

4. An ovule of the plant of claim 2.

5. A tissue culture of regenerable cells from the plant of claim 2.

6. The tissue culture according to claim 5, wherein said cell of the tissue culture are produced from a tissue selected from the group consisting of leaves, pollen, embryos, cotyledon, hypocotyl, meristematic cells, roots, root tips, anthers, flowers, seeds, stems, and suckers.

7. A protoplast produced from the tissue culture of claim 5.

8. A celery plant regenerated from the tissue culture of claim 5, wherein the celery plant has all of the morphological and physiological characteristics of celery cultivar ADS-1, representive seed of said celery cultivar ADS-1 having been deposited under ATCC Accession No. PTA-6041.

9. A method for producing a hybrid celery seed comprising crossing a first parent celery plant with a second parent celery plant and harvesting the resultant hybrid celery seed, wherein said first parent celery plant or said second parent celery plant is the celery plant of claim 2.

10. A method of producing an herbicide resistant celery plant comprising transforming the celery plant of claim 2 with a transgene that confers herbicide resistance.

11. An herbicide resistant celery plant produced by the method of claim 10.

12. A method of producing an insect resistance celery plant comprising transforming the celery plant of claim 2 with a transgene that confers insect resistance.

13. An insect resistant celery plant produced by the method of claim 12.

14. A method of producing a disease resistance celery plant comprising transforming the celery plant of claim 2 with a transgene that confers disease resistance.

15. A disease resistance celery plant produced by the method of claim 14.

* * * * *